United States Patent [19]

Penny

[11] Patent Number: 4,594,200
[45] Date of Patent: Jun. 10, 1986

[54] COMPOSITIONS FOR INCREASING HYDROCARBON PRODUCTION FROM SUBTERRANEAN FORMATIONS

[75] Inventor: Glenn S. Penny, Duncan, Okla.

[73] Assignee: Halliburton Company, Duncan, Okla.

[21] Appl. No.: 671,546

[22] Filed: Nov. 15, 1984

[51] Int. Cl.$^4$ ............... E21B 43/22; C07C 143/08
[52] U.S. Cl. ................ 260/512 R; 260/509; 260/513 R; 260/513 N; 260/513 F; 252/8.55 R
[58] Field of Search ............ 252/8.55 D, 8.55 R; 260/512 R, 513 R, 513 N, 513 B, 513 F, 509

[56] References Cited

U.S. PATENT DOCUMENTS

| | | | |
|---|---|---|---|
| 3,228,979 | 1/1966 | Gaertner | 260/513 R |
| 3,642,880 | 2/1972 | Sweeney | 260/512 R |
| 4,014,926 | 3/1977 | Dear | 260/513 N |
| 4,154,753 | 5/1979 | Fielding | 260/513 R |
| 4,208,466 | 6/1980 | Szur | 524/156 |
| 4,209,456 | 6/1980 | Billenstein | 260/458 R |
| 4,408,043 | 10/1983 | Seale | 252/8.55 D |
| 4,431,595 | 2/1984 | Hashimoto | 260/513 N |
| 4,440,653 | 4/1984 | Briscoe | 166/305.1 |

*Primary Examiner*—C. Warren Ivy
*Attorney, Agent, or Firm*—Robert A. Kent

[57] ABSTRACT

The present invention relates to a chemical composition represented by the formula:

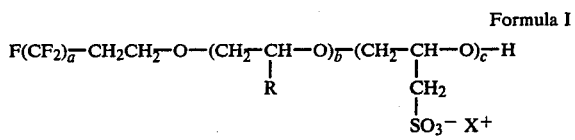

Formula I

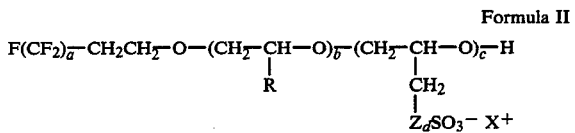

Formula II wherein a is a whole number or fraction thereof in the range of from about 4 to about 18;
wherein b is a whole number or fraction thereof in the range of from about 0 to about 30;
wherein c is a whole number or fraction thereof in the range of from about 1 to about 3;
wherein d is independently a whole number or fraction thereof in the range of from about 0 to about 1 and the sum of the average values of d are less than or equal to c;
R is independently selected from the group consisting of hydrogen and a methyl group whereby mixtures containing both groups may result; and
$X^+$ is an exchangeable cation; and
Z is a nucleophile containing species containing at least one member selected from the group consisting of oxygen and nitrogen wherein the nitrogen is in the form of $NR^1$ wherein $R^1$ is independently selected from the group consisting of hydrogen and methyl radicals.

14 Claims, 2 Drawing Figures

CAPILLARY PRESSURE VS WATER SATURATION IN DOLOMITE COLUMN

COMPOSITIONS FOR INCREASING HYDROCARBON PRODUCTION FROM SUBTERRANEAN FORMATIONS

Various procedures have been developed and utilized heretofore to increase the flow of hydrocarbons from hydrocarbon-containing subterranean formations penetrated by well bores. For example, a commonly used production stimulation technique involves creating and extending fractures in the subterranean formation to provide flow channels therein through which hydrocarbons flow from the formation to the well bore. The fractures are created by introducing a fracturing fluid into the formation at a flow rate which exerts a sufficient pressure on the formation to create and extend fractures therein. Solid fracture proppant materials, such as sand, are commonly suspended in the fracturing fluid so that upon introducing the fracturing fluid into the formation and creating and extending fractures therein, the proppant material is carried into the fractures and deposited therein whereby the fractures are prevented from closing due to subterranean forces when the introduction of the fracturing fluid has ceased.

In such formation fracturing and other production stimulation procedures, it is important to leave the formation with maximum permeability or conductivity whereby hydrocarbons contained in the formation flow to the well bore with the least possible restriction. In order to achieve maximum conductivity of hydrocarbons from subterranean formations, whether or not such formations have been fractured or otherwise stimulated, it has heretofore been the practice to cause the formation surfaces to be water wet. Such water wetting has been shown to provide an improved flow of hydrocarbons through flow channels and capillaries in the magnitude of about three times greater than when the formation surfaces are hydrocarbon wet.

The water wetting of solid surfaces in subterranean hydrocarbon-containing formations as well as the surfaces of solid proppant material deposited therein has heretofore been accomplished using surfactants whereby a layer of water or water and surfactant is spread over the solid surfaces. Such layers of water or water and surfactant are extremely viscous near the interface of the layer and the solid surface, and while the layer provides a slippage or lubricating effect at the interface thereof with hydrocarbons which decreases the resistance to flow, the layer reduces the effective diameter of capillaries and flow channels. This reduction of effective diameter restricts fluid flow, and in very small capillaries or flow channels becomes significant, that is, when the capillary radius is equal to the viscous wetting layer thickness, the flow of hydrocarbons is blocked by the layer.

SUMMARY OF THE INVENTION

By the present invention, methods are provided whereby certain compounds are caused to be adsorbed onto solid surfaces and particularly surfaces of carbonate materials in subterranean hydrocarbon-containing formations in a very thin layer, that is, a layer which is preferably one molecule thick and significantly thinner than a layer of water or a water-surfactant mixture. The compounds so adsorbed on the surfaces resist or substantially reduce the wetting of the surfaces by water and hydrocarbons and provide high interfacial tensions between the surfaces and water and hydrocarbons. This allows the hydrocarbons to displace injected water leaving a lower water saturation and an increased flow of hydrocarbons through capillaries or flow channels in the formations.

DESCRIPTION OF THE PREFERRED EMBODIMENT

Figure 1:
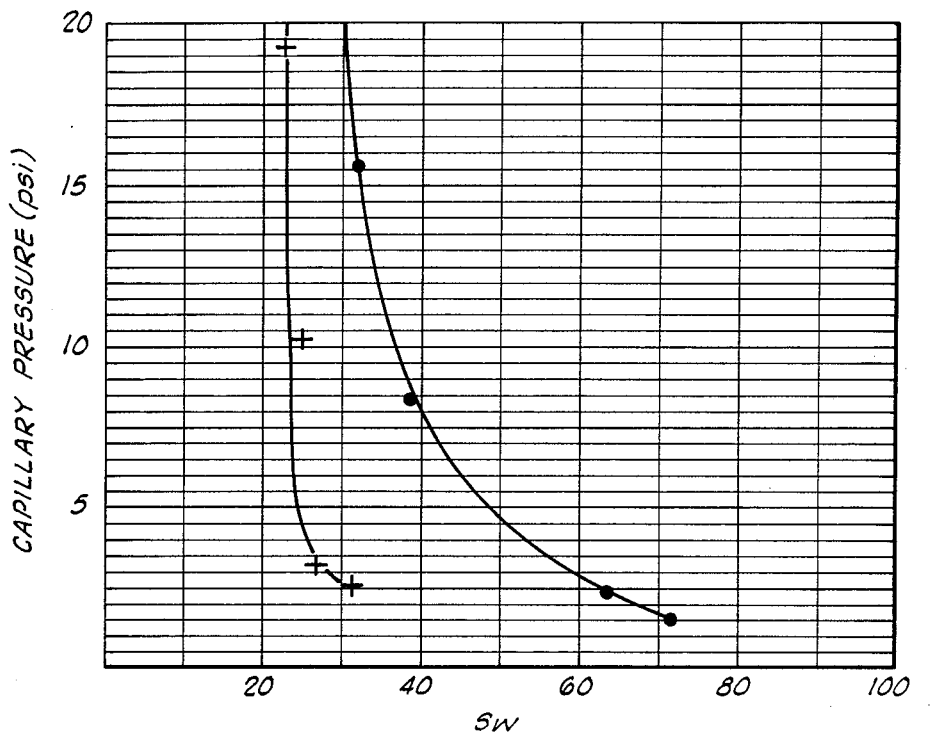
FIG. 1 illustrates a plot of the effectiveness of a perfluoro substituted potassium phenol sulfonate of the present invention in comparison to a conventional treatment fluid.

The compounds which are utilized in accordance with the methods of this invention to reduce the tendency of solid surfaces from becoming water or hydrocarbon wet while not creating significantly thick and/or viscous layers thereon are certain anionic perfluoro compounds and mixtures of such compounds represented by the formula:

Formula I

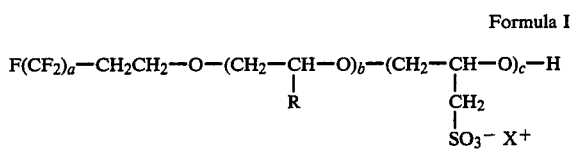

Formula II

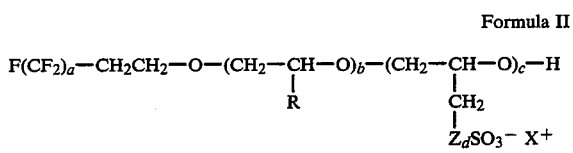

wherein a is a whole number or fraction thereof in the range of from about 4 to about 18;

wherein b is a whole number fraction thereof in the range of from about 0 to about 30;

wherein c is a whole number or fraction thereof in the range of from about 1 to about 3;

wherein d is independently a whole number or fraction thereof in the range of from about 0 to about 3 and the sum of average values of d are less than or equal to c;

R is independently selected from the group consisting of hydrogen and a methyl group whereby mixtures containing both groups may result;

$X^+$ is substantially any exchangeable cation such as those selected from the group consisting of sodium, potassium and ammonium ions or the like or any other cation which does not adversely react to the detriment of the method of the present invention; and Z, when present, is a nucleophile containing species containing either oxygen in combination with the sulfonate radical, such as, for example, phenol sulfonic acid or isethionic acid or nitrogen in the form of $NR^1$ wherein $R^1$ is selected from either hydrogen or methyl radicals, such as, for example, N methyl-taurine sulfonate.

The phrase "whole number or fraction thereof" as used herein indicates that the formula may represent an admixture of compounds wherein the average values of a, b, c and d can be any number in the range set forth such as 2 or 8 or 10 or a fraction such as 2.1, 8.5, 8.8 or 10.2 and the like.

Preferably, in the above formulas,
a is in the range of from about 6 to about 12;
b is in the range of from about 0 to about 20;
c is in the range of from about 1 to about 2;
R is independently selected from hydrogen and methyl radicals; and
X+ is a cation selected from the group consisting of sodium, potassium and ammonium ions or the like.

The preferred perfluoronated compound for use in accordance with the present invention is that represented by the following formula:

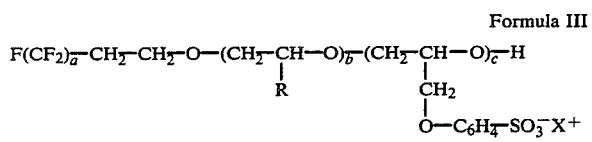

Formula III

In this preferred perfluoronated compound,
a is a whole number or fraction thereof in the range of from about 6 to about 12;
b is a whole number or fraction thereof in the range of from about 10 to about 20;
c is a whole number or fraction thereof in the range of from about 1 to about 2;
R is independently selected from hydrogen and methyl radicals and, preferably, is a methyl radical; and
X+ is a cation selected from sodium, potassium and ammonium ions.

Of this group of compounds, the most preferred is where
a is a whole number or fraction thereof in the range of from about 7 to about 9 and, most preferably, about 8;
b is a whole number or fraction thereof in the range of from about 15 to about 20;
c is about 1.5;
R is independently selected from hydrogen and methyl radicals and, most preferably, methyl; and
X+ is a cation selected from sodium, potassium and ammonium ions and, most preferably, potassium and ammonium ions.

In carrying out the methods of the present invention, the anionic perfluoro compound or compounds can be applied directly to a subterranean formation whereby the surfaces thereof are contacted by the compounds and adsorbed thereon. Preferably, the anionic perfluoro compound or compounds utilized are dissolved or dispersed in a carrier fluid which is in turn introduced into the formation whereby the carried anionic perfluoro compounds are distributed in the formation and contact solid surfaces therein whereby they are adsorbed thereon. Aqueous or hydrocarbon base carrier fluids can be utilized in the form of liquids, foams, emulsions and so forth. The aqueous fluid can comprise, for example, acidic solutions containing acids such as, for example, hydrochloric acid, acetic acid, formic acid and mixtures thereof or salt solutions such as KCl, NH4Cl or NaCl or fresh water. The carrier fluid also can contain other conventional additives which are compatible with the anionic perfluoro compound of the present invention such as, for example, nonemulsifying agents or surface tension reducing agents, mutual solvents, corrosion inhibitors, gelling agents, paraffin and iron control agents and the like. The particular quantity of perfluoro compounds combined with the carrier fluid can vary widely depending upon the type of formation to be treated and other factors, but generally the anionic perfluoro compounds utilized are combined with the carrier fluid in an amount in the range of from about 0.01% to about 0.2% by weight of the carrier fluid. It is to be understood that larger quantities can be employed but such use is economically undesirable.

In carrying out subterranean formation fracturing processes wherein a fracturing fluid is introduced into a subterranean formation at a rate such that fractures are created in the formation and extended therein, the anionic perfluoro compound or compounds utilized are conveniently combined with the fracturing fluid prior to introducing it into the formation.

In the usual case, a non-viscous preflush solution is injected into the formation, followed by a viscous fracturing fluid without proppant material which is in turn followed by a viscous fracturing fluid carrying solid proppant material, such as sand, bauxite, glass beads or the like. The fracturing fluids create and extend fractures in the formation and the solid proppant material is carried into and deposited in the fractures. In carrying out such fracturing procedures in accordance with this invention, the anionic perfluoro compound or compounds utilized can be dissolved or dispersed in the non-viscous preflush solution as well as the viscous fracturing fluids in a convenient manner. Upon introducing the preflush and fracturing fluids into the subterranean formation, the anionic perfluoro compounds are adsorbed on the solid surfaces of the formation. Thus, the carbonate-containing surfaces of the formation have anionic perfluoro compounds adsorbed thereon whereby such surfaces are substantially prevented from being wetted by water or hydrocarbons and the flow of hydrocarbons through the formation is significantly increased.

In subterranean formation fracturing procedures, cationic perfluoro compounds discussed in U.S. Pat. No. 4,425,242 can be combined with the proppant-laden fluids introduced into the formation in a sufficient quantity whereby the compounds are adsorbed on the proppant material employed if such proppant material has not been pretreated. This quantity can vary depending upon the type of formation and the quantity of proppant material utilized, but generally is in the range of from about 0.01% to about 0.2% by weight of the fracturing fluid and proppant material used.

The Starting Perfluoro Alcohol Compounds

The starting perfluoro compounds which are used to generate perfluorinated substituents within the compositions of this invention are derived from perfluoro substituted ethanols which are represented by the following formula:

  Formula IV

In the above Formula IV, a has the numerical values previously indicated in Formulas I and II. A preferred perfluoro ethanol is commercially obtained from E.I. duPont de Nemours & Co. under the commercial name "Zonyl BA". This material is generally described by Formula IV wherein a is from about 6 to about 12 and wherein the average a is equal to about 8. An average a, again, indicates that the compounds used may be an admixture of molecules wherein a is individually 6, 8, 10 or 12 and the like with the numerical average being about 8.

The Oxiranes and Substituted Oxiranes

The starting oxirane and substituted oxirane used to initially react with the perfluorinated alcohols previously described are chosen from the group consisting of ethylene oxide, propylene oxide, butylene oxide and mixtures thereof. The preferred oxirane reactants are chosen from the group consisting of ethylene oxide, propylene oxide and mixtures thereof added sequentially or via mixer addition. The most preferred oxirane reactant is propylene oxide.

The Epihalohydrins

The starting epihalohydrins used to react with the perfluoronated alcohol adducts with the oxirane compounds previously described are chosen from the group consisting of epichlorohydrin, epibromohydrin and epiiodohydrin. The preferred epihalohydrin is epichlorohydrin.

The Sulfonates

The starting compounds used to form the compounds of the present invention can comprise, for example, sodium, potassium or ammonium sulfite which when reacted with the epihalohydrin forms a sulfonate, or the previously formed sulfonates of isethionic acid or N-methyl taurine. Likewise, the starting compound can be a phenol or aniline which has been sulfonated previously such as, for example, phenol sulfonic acid and the like.

The Catalysts

The catalysts used in the reactions of the perfluoro alcohol previously described, the oxirane and substituted oxirane compounds previously described, and the epihalohydrins described above are chosen from Lewis acid compounds. These catalysts are represented by antimony pentachloride, boron trichloride, boron trifluoride, stannic chloride, ferric and ferrous chloride and the like. The Lewis acid preferred in both the reaction between the perfluoro alcohol and the oxirane compounds, as well as between the alkoxylate adduct formed by this first reaction and the epihalohydrin is antimony pentachloride. The catalyst is used at a concentration ranging from 0.01% based on the final adduct up to about 1.0% by weight based on the final adduct weight. A preferred range of catalyst is between 0.1% and 0.5% by weight based on the final adduct. A most preferred catalyst concentration, particularly in reference to the use of antimony pentachloride is between 0.2 and 0.4% by weight of the final adduct obtained from this combined reaction.

Reaction Conditions, Synthesis of Perfluoro Alcohol/Oxirane Compounds

The initial alkoxylate adducts required to manufacture the compounds of this invention are synthesized by reacting the perfluoro alcohol described above with the oxirane and substituted oxirane compounds described above. This first reaction is done under anhydrous conditions and is catalyzed by a Lewis acid catalyst, again described above. After this initial alkoxylate adduct is formed, it is then reacted with an epihalohydrin to obtain the final adduct.

The reaction of the perfluoro alcohol with the oxirane and substituted oxiranes is accomplished by using the following method or variations thereof.

To an autoclave which has previously been charged with the perfluoro alcohol and a Lewis acid catalyst, an amount of an oxirane or substituted oxirane or a mixture thereof is added at such a rate so as to maintain a reaction temperature between 60° and 140° C. The reaction is catalyzed by a Lewis acid, preferably antimony pentachloride, and additional catalyst may be added simultaneously with the addition of the oxirane/substituted oxirane compounds. The oxirane/substituted oxirane compounds may be added in such quantities such that the molar ratio of perfluoro alcohol to oxirane/substituted oxirane compounds is between 1:4 and 1:10, and a most preferred molar ratio is between 1:6 and 1:8. The reaction rate may be controlled by using a combination of temperature and catalyst concentration variations.

Once the oxirane/substituted oxirane compounds are completely charged to the autoclave, the autoclave is maintained at a temperature of at least 80° C. until the reaction is completed. It is preferred that the autoclave be maintained at temperatures of at least 100° C. for a time period of at least 30 minutes following the completed addition of the oxirane/substituted oxirane chosen. The autoclave may be cooled and a sample may be removed for analysis or for further chemical reaction. Additional oxirane/substituted oxirane also may be charged to the autoclave to obtain higher molecular ratios of perfluoro alcohol and oxirane/substituted oxirane or to vary the type of oxirane/substituted oxirane substitution in the final product. The reaction may be conveniently monitored by analyzing unreacted oxiranes using Gas Chromatographic techniques. The most preferred adduct is obtained when residual oxirane levels are about 0.2 weight percent or below.

Alternatively, the autoclave may be maintained at reaction temperature while additional catalyst and the epihalohydrin chosen to obtain the final adduct is added to the autoclave contents. The preferred final adduct is again obtained when residual epihalohydrin levels are about 0.2 weight percent or below as is conveniently monitored by using Gas Chromatographic techniques. All of the above reactions are anhydrous in nature and are accomplished in an inert atmosphere such as is obtained by a nitrogen environment.

Reaction Conditions; Synthesis of Perfluoro Alcohol/Oxirane-Substituted Oxirane/Epihalohydrin Adduct Once the initial alkoxylated adduct is formed using reaction conditions described above, or variations thereof, the autoclave may be cooled and the initial alkoxylated adduct removed for further reactions. As above, the initial adduct may be reacted with quantities of epihalohydrin such that the desired molar ratios represented in Formulas I and II above may be obtained. Again, reaction conditions are anhydrous, in an inert environment such as may be obtained with a nitrogen atmosphere, under Lewis acid catalyst conditions previously described, and are best obtained by the addition of the chosen epihalohydrin, such as epichlorohydrin, to an autoclave containing the previously reacted compound derived from the reaction of perfluoro alcohol and the oxirane/substituted oxirane compounds.

The reaction temperatures are preferably maintained below 120° C. and the Lewis acid catalyst is preferably used at a concentration of at least 0.1% based on the weight of the expected final product. The preferred catalyst is, again, antimony pentachloride, although $BF_3$ etherate also may be readily used. The antimony pentachloride gives fewer side reaction products and is most preferred as a catalyst for this reaction.

The addition of epihalohydrin is maintained at a rate to control the reaction temperature below 120° C., preferably within a range between 60° and 100° C. After epihalohydrin addition is completed, the reactants are heated for at least an additional 30 minutes at a temperature of about 100° C. so as to obtain complete reaction. As required, additional catalyst may be added so as to enhance the reaction rate leading to final and complete reaction of all reactants. Additional epihalohydrin may be added so as to increase the mole ratio of the final product obtained through this reaction. When the preferred adduct is obtained, such as, the adduct represented by Formulas I or II above, the sulfonation reaction may be commenced in the same autoclave or may be commenced by cooling the autoclave contents, isolating the contents or a portion thereof, and reacting this product with one of the appropriate sulfonating agents or sulfonate containing reactants previously described.

Reaction Conditions, The Sulfonation Reaction

The reaction between the perfluoro alcohol/oxirane-substituted oxirane/epihalohydrin adduct and the sulfonate may be conducted using either one of the following methods as well as any other method which results in the desired reaction.

The epihalohydrin adduct of the oxirane substituted perfluoro alcohol is isolated in a reaction vessel and diluted to about a 50 percent active solution utilizing a 50:50 mixture by weight of isopropanol and water. An equimolar amount of an aqueous solution of sodium or ammonium bisulfite is added to the reaction vessel and the mixture is stirred at ambient temperature for about one hour. This procedure produces a sulfonate through dehydrohalogenation and sulfite addition.

Alternatively, the epihalohydrin adduct of the oxirane substituted perfluoro alcohol is diluted to about a 33 percent active solution utilizing a 50:50 mixture by weight of isopropanol and water and placed in an autoclave. An equivalent of phenol sulfonic acid, taurine sulfonate or sulfonated aniline then is admixed with the diluted mixture. The acid then is neutralized with an equivalent of potassium carbonate. When the acid is phenol sulfonic acid, an additional equivalent of potassium carbonate is added to the mixture to form a phenolate anion. The phenolate or amines present react with the epihalohydrin adduct to form the desired sulfonate derivative upon stirring the mixture in the autoclave for about two hours at a temperature of about 125° C.

EXAMPLES

I. Alkoxylates—the formation of the initial adduct between the perfluoro alcohol and the oxirane/substituted oxirane compounds.

A. Ethylene Oxide (EO)

EXAMPLE 1

To a PARR autoclave is added 485 grams (1 mole) Zonyl BA alcohol and 1 cc of antimony pentachloride. The autoclave was closed and heated to 50° C. Three hundred fifty-two (352) grams (approximately 8 moles) of ethylene oxide was slowly added to the autoclave, the addition rate being controlled in such a manner as to maintain the reaction temperature below 100° C. After at least ½ of the EO was added, the addition rate was increased in such a manner as to allow the reaction temperature to slowly rise to 140° C. After the addition of ethylene oxide was completed, the autoclave temperature was maintained at 130°-140° C. for one hour. The contents of the autoclave were then cooled and removed from the autoclave. The reaction product is the mixed alkoxylate expected from the addition of 8 moles of ethylene oxide to 1 mole of the Zonyl BA perfluoro alcohol.

EXAMPLE 2

Four hundred eighty-five (485) grams of the Zonyl BA alcohol and 1 cc of antimony pentachloride was added to an autoclave and heated to 50° C. Four hundred forty (440) grams (10 moles) of EO was added slowly so as to maintain reaction temperature below 100° C. Reaction temperature may be controlled by the addition rate of EO or by adjusting the rate of cooling of the PARR autoclave using external cooling coils. After about ⅓ of the ethylene oxide was added, the reaction temperature was allowed to rise to 140° C. After the addition of EO was completed, the reaction vessel temperature was maintained between 130°-140° C. for approximately one hour by heating this reaction vessel. The content were cooled and removed from the autoclave. The reaction product is that expected from the 10 mole addition of ethylene oxide to the Zonyl BA perfluoro alcohol previously described.

EXAMPLE 3

The conditions of Examples 1 and 2 were repeated except that 15 moles of ethylene oxide were added at such a rate as to control the reaction temperature below 140° C. The product mix obtained was that expected from the 15 mole addition of ethylene oxide to the perfluoro alcohol.

B. Propylene Oxide (PO)

EXAMPLE 4

To an autoclave was added 485 grams (1 mole) of the Zonyl BA perfluoro alcohol. The autoclave was purged with nitrogen and 2 cc of antimony pentachloride was added. The autoclave was closed to the atmosphere and heated to 50° C. while stirring. Two moles (about 108 grams) of PO was slowly added to the reaction vessel at a rate sufficient to maintain the reaction temperature below 100° C. Addition of the propylene oxide required approximately one hour. The autoclave contents were then heated for another hour at a temperature of 90° C. The reactor was cooled and approximately 666 grams of this 2 mole adduct of the perfluoro alcohol/propylene oxide alkoxylate was removed for further reaction.

EXAMPLE 5

To the materials remaining in the autoclave from Example 4 was added 108 grams of additional propylene oxide. The initial temperature at the start of the reaction was 52° C. The vessel was depressurized and another 0.5 mls of antimony pentachloride catalyst was added. Addition of the propylene oxide was reinitiated. The temperature of the reaction vessel was less than 80° C. throughout the addition of propylene oxide. The heat source was turned off and the autoclave allowed to cool overnight. The next day, the contents of the autoclave were determined to be the 4 mole adduct of propylene oxide of the perfluoro alcohol.

EXAMPLE 6

Three hundred (300) grams of the alkoxylate adduct obtained from Example 4 was charged to a PARR autoclave along with 5/8 cc of antimony pentachloride. The reactor was purged with nitrogen and heated to 50° C. Addition of propylene oxide was begun. Sufficient propylene oxide was added to the reactor to obtain a 6 mole propylene oxide adduct onto the perfluoro alcohol. The propylene oxide addition rate was maintained so as to control the reaction temperature below 100° C. during the addition of propylene oxide. The reaction vessel was heated for an additional hour after the addition of propylene oxide was completed at a temperature of 100° C. The reaction vessel was cooled and the 6 mole adduct of the perfluoro alcohol was removed from the reactor.

EXAMPLE 7

Three hundred (300) grams of the adduct from Example 4 was charged to a PARR autoclave along with 1 milliliter of antimony pentachloride. The same precautions were taken as in Example 6 to maintain reaction temperatures and to maintain a nitrogen atmosphere. Sufficient propylene oxide was added to obtain a 10 mole propylene oxide adduct of the Zonyl BA perfluoro alcohol.

C. Mixed Oxide Alkoxylate

EXAMPLE 8

To a PARR autoclave was added 485 grams (1 mole) perfluoro alcohol and 2 milliliters of antimony pentachloride. The reactor was purged with nitrogen and closed to the atmosphere. The reactor contents were heated to 50° C. while they were being stirred. Ten moles of ethylene oxide were slowly added to the reactor contents at a rate sufficient to maintain the temperature of the reactor below 100° C. The reactor was heated at a temperature of 100° C. for 1.5 hours after the addition of all of the ethylene oxide. After this heating period, 5 moles of propylene oxide were slowly added so as to maintain the reactor temperature at 100° C. The reactor contents were then agitated for an additional hour and the temperature was allowed to rise slowly to 130° C. The temperature was maintained at 130° C. for an hour after all the ethylene oxide had been added. The autoclave was cooled and approximately 1,220 grams of the final alkoxylate adduct were recovered, demonstrating essentially 100% recovery.

II. The Reaction Between Alkoxylates and Epihalohydrin.

EXAMPLE 9

To an autoclave was added 485 grams of Zonyl BA perfluoro alcohol and 2 milliliters of antimony pentachloride catalyst. The autoclave was purged with nitrogen and closed to the atmosphere. The autoclave was heated to 60°-70° C. for about 30 minutes. A mixture of 330 grams of ethylene oxide and 442 grams of propylene oxide was slowly added to the stirred contents of the autoclave. The addition rate of this mixed oxide solution was controlled such that the temperature never exceeded 90° C. and, in fact, remained in the 75°-85° C. range. The temperature was maintained for about 90 minutes after the addition of the mixed oxide was complete.

To the contents of the PARR autoclave was then added 170 grams or approximately 1.5 moles of epichlorohydrin. hydrin. The same reaction conditions and temperature ranges were maintained as above. An additional 60 minutes of reaction time was allowed after the addition of epichlorohydrin was complete so as to complete the reaction between the epichlorohydrin and the mixed alkoxylate obtained in the previous reaction step.

EXAMPLE 10

Two hundred four (204) grams of an 8 mole EO adduct of the Zonyl BA perfluoro alcohol and 0.25 milliliter of $BF_3$ etherate were placed in a 500 milliliter flask. The flask was equipped with a condenser, a stirrer, a thermometer, and a pressure equalized dropping funnel. This mixture was heated to 50° C. and a nitrogen purge was initiated. Dropwise addition of epichlorohydrin was started. The reaction temperature was held between 55°-60° C. by regulating the rate of addition of epichlorohydrin. Approximately 34.5 grams of epichlorohydrin was added to the flask contents over a period of one hour. The reaction contents were postheated for approximately 1.5 hours, then cooled and removed from the flask. The product was an adduct of the perfluoro alcohol/8 mole ethylene oxide/1.5 mole epichlorohydrin. Product yield as judged by the weight of recovered material is 98+%.

EXAMPLE 11

Into 3 separated flasks equipped as in Example 10, products from section I.B., Examples 4, 5 and 6, were independently charged. Sufficient $BF_3$ etherate was added to the contents of each flask and the flasks heated to approximately 50° C. Nitrogen purges were started on each flask. Epichlorohydrin was added to each flask so as to yield a 2 mole epichlorohydrin adduct to the materials obtained from Example 4, and a 1.5 mole epichlorohydrin adduct from both the materials of Examples 5 and 6. The epichlorohydrin was added at a rate which maintained the temperature of each reaction vessel at less than 95° C. Again each reaction vessel was postheated for approximately one hour at temperatures not exceeding 95° C. The products obtained in each case were respectively those expected from (1) a 1:2:2 mole adduct of perfluoro alcohol/propylene oxide/epichlorohydrin; (2) a 1:4:1.5 mole adduct of perfluoro alcohol/propylene oxide/epichlorohydrin; and (3) a 1:6:1.5 mole adduct of perfluoro alcohol/propylene oxide/epichlorohydrin adduct.

EXAMPLE 12

One mole of a product obtained from following the first step of Example 9 is added to a 500 ml flask equipped as above. Sufficient epibromohydrin to obtain a 1 mole adduct is slowly added to this material after it is heated to approximately 50° C. and 1 milliliter of antimony pentoxide is added to the flask. The epibromohydrin addition rate is controlled such that the reaction temperature never exceeds 100° C. The product expected is a 1:2:2:1.0 molar adduct of perfluoro alcohol/ethylene oxide/propylene oxide/ and epibromohydrin.

III. The Sulfonation Reaction.

EXAMPLE 13

To a reaction flask was added the 8 mole ethylene oxide adduct of Zonyl BA perfluoro alcohol of Example 10. The adduct was dissolved in a 50:50 mixture by weight of isopropanol and water in an amount sufficient to provide about a 33 percent active solution. To the diluted mixture was added an equimolar amount of sodium bisulfite in the form of about a 40 percent aqueous solution. The mixture then was stirred for about one hour at ambient temperature. The resulting product was found to be the isopropyl sulfonate ether of the 8 mole ethylene oxide adduct of Zonyl BA perfluoro alcohol.

EXAMPLE 14

To a reaction flask was added a quantity of a 4 mole ethylene oxide adduct of Zonyl BA perfluoro alcohol prepared in accordance with the foregoing procedures. The adduct is dissolved in a 50:50 mixture by weight of isopropanol and water in an amount sufficient to provide about a 30 percent active solution. To the diluted mixture was added an equimolar amount of N-methyl taurine. The contents of the reaction flask then were heated to a temperature of about 60° C. and refluxed for about one hour. The resulting product was found to be the isopropyl-N-methyl taurine sulfonate ether of the 4 mole ethylene oxide adduct of Zonyl BA perfluoro alcohol.

EXAMPLE 15

To a reaction flask was added the 10 mole ethylene oxide adduct of Zonyl BA perfluoro alcohol prepared in Example 2. The adduct was reacted with 1.5 moles of epichlorohydrin as previously described and the resulting oxirane epichlorohydrin adduct of Zonyl BA perfluoro alcohol then was diluted with dimethyl sulfoxide in a ratio of adduct to sulfoxide of 1 to 3. To the diluted mixture in the reaction flask was added a molar equivalent of potassium phenol sulfonate. The contents of the flask then were heated to about 38° to 40° C. for about one hour. The resulting product, as expected, was found to be the isopropyl potassium phenol sulfonate ether of the 10 mole ethylene oxide adduct of Zonyl BA perfluoro alcohol.

EXAMPLE 16

To a reaction flask was added a quantity of an 8 mole propylene oxide adduct of Zonyl BA perfluoro alcohol prepared in accordance with the foregoing procedures. The adduct was dissolved in the flask in a 75:25 mixture by weight of isopropanol and water in an amount sufficient to provide about a 33 percent active solution. To the mixture in the flask then was added an equimolar amount of sulfanilic acid. The contents of the reaction flask then were heated to a temperature of about 60° C. and refluxed for about 1 hour. The resulting product was, as expected, found to be the isopropyl sulfanilic acid adduct of the 8 mole propylene oxide adduct of the Zonyl BA perfluoro alcohol.

EXAMPLE 17

To a Parr autoclave was added the 10 mole ethylene oxide/5 mole propylene oxide adduct of Zonyl BA perfluoro alcohol of Example 8. The adduct was dissolved in a 50:50 mixture by weight of isopropanol and water in an amount sufficient to provide about a 33 percent active solution. To the diluted mixture was added one equivalent of phenol sulfonic acid and two equivalents of potassium carbonate. The mixture then was heated to a temperature of about 125° C. for about two hours. The resulting product was found to be as expected the isopropyl phenol potassium sulfonate ether of the 10 mole ethylene oxide/5 mole propylene oxide adduct of Zonyl BA perfluoro alcohol.

EXAMPLE 18

To a Parr autoclave was added a quantity of a 15 mole mixed ethylene oxide and propylene oxide adducts of Zonyl BA perfluoro alcohol. The adducts were dissolved in a 75:25 mixture by weight of isopropanol and water in an amount sufficient to provide about a 33 percent active solution. To the diluted mixture was added one equivalent of phenol sulfonic acid and two equivalents of potassium carbonate. The contents of the autoclave then were heated to a temperature of about 125° C. for about two hours. The resulting product was found to be, as expected, the isopropyl phenol potassium sulfonate ether of the 15 mole mixed ethylene oxide/propylene oxide adduct of Zonyl BA perfluoro alcohol.

In order to facilitate a clear understanding of the methods of the present invention, the following examples are provided.

EXAMPLE 19

To illustrate the effectiveness of the compositions of the present invention in enhancing liquid and gaseous hydrocarbons permeability in a limestone matrix and improving the return of treating fluids by lowering capillary pressure, the following tests were performed. The tests utilize a dolomite column which is treated with fluids containing the composition of the present invention in an amount of from about 0.01 to about 0.1 percent by weight. The percent treating fluid recovered at hydrocarbon breakthrough is measured and the water saturation of the dolomite column, at each flowing pressure is calculated to permit the preparation of a plot of capillary pressure versus water saturation. FIG. 1 illustrates a plot of the effectiveness of a perfluoro substituted potassium phenol sulfonate of the present invention (Formula II: a=8, b=0, c=1, Z=oxygen and d=1) in comparison to a conventional treatment utilizing 2% KCl. The treatment with 2% KCl results in about a 28 percent recovery of treating fluid at oil breakthrough in the column while the use of the composition of the present invention in a 0.01 percent concentration provides about a 90 percent recovery of treating fluid at oil breakthrough. Also, the presence of the composition of the present invention dramatically shifts the capillary pressure curve as illustrated in FIG. 1. While the 2% KCl exhibits a capillary pressure of about 20 psi at about 30 percent water saturation ($S_w$), the column treated with the composition of the present invention exhibits a capillary pressure of about 2.5 psi at about 30 percent $S_w$.

A final measurement of overall treatment effectiveness is the effective permeability of the formation to hydrocarbon flow at each equilibrium water saturation. For example, the control sample comprising 2% KCl utilized in the oil flow experiment provided a relative permeability to oil ($k_o$) of about 3.49 at a 1.0 cc/min flow rate and about 5.18 at 10 cc/min. By way of contrast, the use of the composition of the present invention in the treatment of a carbonate-containing formation results in an effective permeability that significantly exceeds that of the control fluid and commonly available surfactants. Further, the percentage of treating fluid recovered at hydrocarbon breakthrough is maximized by use of the composition of the hydrocarbon breakthrough is maximized by use of the composition of the present invention. For example, the composition of the present invention previously identified (Formula II: a=8, R=hydrogen, b=0, c=1.5, Z=oxygen and d=1) provided 100 percent treating fluid recovery and a $k_o$ of about 7.57 at 10 cc/min. In the gas flow experiments, a composition of the present invention (Formula III: a=8, R=CH$_3$, b=15, c=1.5 and Z=oxygen) resulted in a treating fluid recovery of about 85 percent while a $k_g$ of 4.23 was achieved at 10 psi gas pressure.

Figure 2:
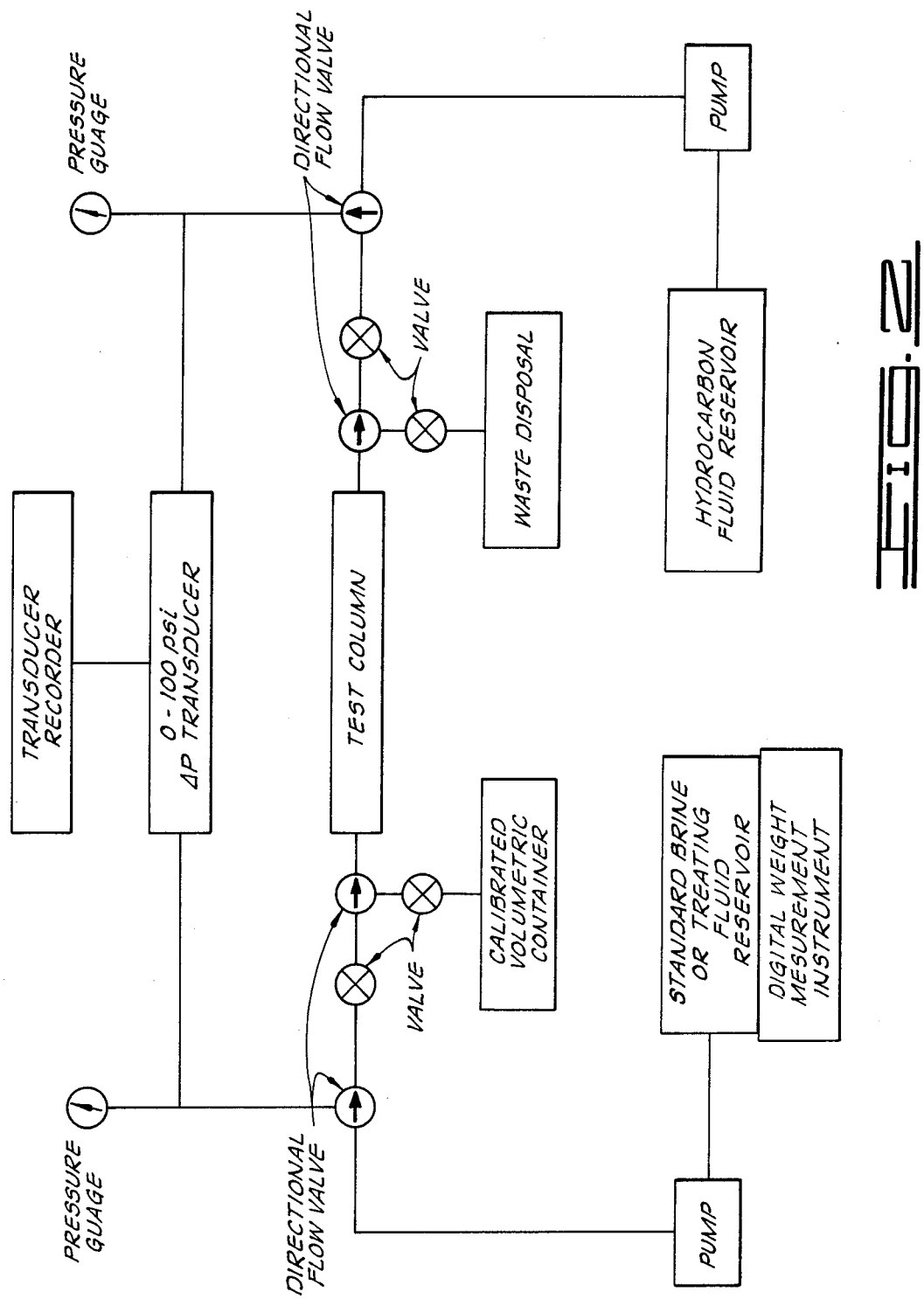
FIG. 2 is a diagrammatic illustration of the test apparatus employed in evaluating the performance of various compositions in increasing hydrocarbon production.

Test Procedure:

A packed column having a ¾″ O.D. and about 12 in. length is prepared with sieved 100–200 mesh dolomite and placed in the test system illustrated in FIG. 2. API standard brine is flowed into the packed column at a rate of 1.0 cc/min until the column is saturated. The time required to achieve saturation is about 10 minutes. The pore volume of the packed column then is determined by well known techniques.

For experimental tests utilized in the determinations of oil breakthrough, a refined hydrocarbon oil then is flowed through the packed column in the reverse direction to prior brine flow at a rate of 1.0 cc/min to obtain a residual water saturation level within the column. Thereafter, one pore volume of the treating fluid containing 0.01 percent by weight of the designated composition of the present invention is flowed into the column in the same direction as the previously introduced brine at a rate of 1 cc/min. The treating fluid also contained 2% KCl and a nonemulsifier consisting of an alkoxylated phenol formaldehyde resin and various ethoxylated components. A quantity of the refined oil then is flowed in the opposite direction of the treating fluid at sequential rates of about 0.5 cc/min, 1.0 cc/min, 5.0 cc/min and 10.0 cc/min for two hours at each rate. The volume of brine and treating fluid recovered and the pressure is measured at each of the various flow rates as well as the percent of the treating fluid recovered at oil breakthrough. The equilibrium water saturation within the packed column and the relative oil permeability then are calculated at each oil flow rate by known techniques.

For experimental tests utilized in the determination of gas breakthrough, nitrogen gas is flowed through the brine saturated packed column at 10 psi pressure in the reverse direction to prior brine flow to obtain a residual water saturation level within the column. The column then is treated with the composition of the present invention as previously described together with an amphoteric surface tension reducing agent and a mutual solvent. The flow of nitrogen gas through the packed column then is resumed in the opposite direction of the treating fluid at sequential pressures of 1.0, 2.0, 5.0 and 10 psi for two hours at each rate. The fluid recovered and gas flow rate at each pressure is determined as well as the percent of the treating fluid recovered at gas breakthrough. The equilibrium water saturation within the packed column then and the effective permeability to gas are calculated at each pressure level of the sequential gas flows.

The effectiveness of the various perfluoro-substituted anionic compounds of the present invention in lowering capillary pressure and improving aqueous treatment fluid recovery and hydrocarbon permeability in limestone matrices is summarized in Table I and Table II, below.

TABLE I

Water Recovery and Capillary Pressure Measurements Employing Perfluoro-Substituted Sulfonates in Oil

| Composition | Water Recovery at Oil Breakthrough (% Treatment Fluid) | (Sw) | Oil Flow (cc/min) | (Δ P) | (Sw) | $k_o$ |
|---|---|---|---|---|---|---|
| 2% KCl | 28 | 72 | 0.5 | 1.56 | 71.0 | 2.60 |
| | | | 1.0 | 2.32 | 63.7 | 3.49 |
| | | | 5.0 | 8.42 | 38.2 | 4.80 |
| | | | 10.0 | 15.62 | 32.0 | 5.18 |
| Formula III: (a=8, R=hydrogen, b=0, c=1.5) | 100 | 36 | 0.5 | 2.7 | 31.0 | 1.50 |
| | | | 1.0 | 3.2 | 27.0 | 2.53 |
| | | | 5.0 | 7.6 | 26.0 | 5.32 |
| | | | 10.0 | 10.7 | 26.0 | 7.57 |
| Formula III: (a=8, R=hydrogen, b=15, c=1.5) | 78 | 52 | 0.5* | 21.0 | 50.0 | 0.19 |
| | | | 1.0 | 40.0 | 44.0 | 0.20 |
| | | | 4.0 | 180.0 | 40.0 | 0.18 |
| Formula III: (a=8, R=CH$_3$, b=8, c=1.5) | 89 | 47 | 0.5* | 90.0 | 47.0 | 0.04 |
| | | | 1.0 | 190.0 | 39.0 | 0.04 |
| | | | 2.0 | 310.0 | 36.0 | 0.05 |
| Formula III: (a=8, R=CH$_3$, b=15, c=1.5) | 100 | 30 | 0.5 | 2.2 | 20.0 | 1.84 |
| | | | 1.0 | 3.1 | 25.0 | 2.61 |
| | | | 5.0 | 5.3 | 24.0 | 7.64 |
| | | | 10.0 | 12.0 | 22.0 | 6.75 |
| Formula III: (a=8, mixed oxide adduct having order of addition of R=hydrogen b=10 and R=CH$_3$, b=5, c=1.5) | 96 | 41 | 0.5 | 1.63 | 36.0 | 2.48 |
| | | | 1.0 | 2.30 | 32.0 | 3.52 |
| | | | 5.0 | 7.05 | 32.0 | 5.74 |
| | | | 10.0 | 12.40 | 30.0 | 6.53 |
| Formula I: (a=8, R=hydrogen, b=8, c=1.5) | 85 | 39 | 1.0 | 1.88 | 34.0 | 4.30 |
| | | | 0.5 | 2.64 | 36.6 | 1.53 |
| | | | 1.0 | 3.53 | 29.0 | 2.29 |
| | | | 5.0 | 10.23 | 26.7 | 3.95 |
| | | | 10.0 | 19.13 | 26.0 | 4.23 |
| Formula I: (a=8, R=hydrogen, b=10, c=1.5) | 88 | 39 | 1.0 | 1.88 | 34.0 | 4.30 |
| | | | 0.5 | 2.64 | 36.6 | 1.53 |
| | | | 1.0 | 3.53 | 29.0 | 2.29 |
| | | | 5.0 | 10.23 | 26.7 | 3.95 |
| | | | 10.0 | 19.13 | 26.0 | 4.23 |

*Emulsion formed resulting in plugging of column due to incompatibility with selected nonemulsifying agent

TABLE II

Water Recovery and Capillary Pressure Measurements Employing Perfluoro-Substituted Sulfonates in Gas

| Composition | Concentration | % Water Recovery at Gas Breakthrough (%) | (Sw) | P (psi) | (Sw) | $k_g$ |
|---|---|---|---|---|---|---|
| 2% KCl | | 45 | 73 | 1.0 | 89.5 | 0.00 |
| | | | | 2.0 | 55.9 | 1.20 |
| | | | | 5.0 | 43.5 | 2.90 |
| | | | | 10.0 | 31.6 | 3.95 |
| Formula III: (a=8, R=hydrogen, b=0, c=1.5) | .01% | 70 | 66 | 1.0 | 67.0 | 0.00 |
| | | | | 2.0 | 48.0 | 1.33 |
| | | | | 5.0 | 39.0 | 2.43 |
| | | | | 10.0 | 37.0 | 2.89 |
| Formula III: (a=8, R=hydrogen, b=0, c=1.5) | .1% | 69 | 66 | 1.0 | 67.0 | 0.00 |
| | | | | 2.0 | 48.0 | 1.33 |
| | | | | 5.0 | 39.0 | 2.43 |
| | | | | 10.0 | 37.0 | 2.89 |
| Formula III: (a=8, R=hydrogen, b=8, c=1.5) | .1% | 78 | 62 | 1.0 | 76.0 | 0.00 |
| | | | | 2.0 | 73.0 | 0.00 |
| | | | | 5.0 | 44.0 | 0.23 |
| | | | | 10.0 | 30.0 | 0.69 |
| Formula III: (a=8, R=hydrogen, b=15, c=1.5) | .01% | 54 | 73 | 1.0 | 77.0 | 0.00 |
| | | | | 2.0 | 47.0 | 1.56 |
| | | | | 5.0 | 35.0 | 4.27 |
| | | | | 10.0 | 33.0 | 4.32 |

TABLE II-continued
Water Recovery and Capillary Pressure Measurements Employing Perfluoro-Substituted Sulfonates in Gas

| Composition | Concentration | % Water Recovery at Gas Breakthrough (%) | (Sw) | Capillary Pressure Data P (psi) | (Sw) | $k_g$ |
|---|---|---|---|---|---|---|
| Formula III: (a=8, R=hydrogen, b=15, c=1.5) | .1% | 100 | 37 | 1.0 | 52.0 | 0.00 |
| | | | | 2.0 | 50.0 | 0.00 |
| | | | | 5.0 | 37.0 | 0.00 |
| | | | | 10.0 | 29.0 | 0.11 |
| Formula III: (a=8, R=CH$_3$, b=8, c=1.5) | .01% | 52 | 75 | 1.0 | 75.0 | 0.00 |
| | | | | 2.0 | 51.0 | 1.61 |
| | | | | 5.0 | 40.0 | 2.94 |
| | | | | 10.0 | 38.0 | 3.58 |
| Formula III: (a=8, R=CH$_3$, b=8, c=1.5) | .1% | 76 | 63 | 1.0 | 65.0 | 0.00 |
| | | | | 2.0 | 51.0 | 1.33 |
| | | | | 5.0 | 44.0 | 4.00 |
| | | | | 10.0 | 38.0 | 4.46 |
| Formula III: (a=8, R=CH$_3$, b=15, c=1.5) | .01% | 85 | 58 | 1.0 | 60.0 | 0.00 |
| | | | | 2.0 | 42.0 | 2.02 |
| | | | | 5.0 | 36.0 | 3.08 |
| | | | | 10.0 | 30.0 | 4.32 |
| Formula III: (a=8, R=CH$_3$, b=15, c=1.5) | .1% | 85 | 60 | 1.0 | 65.0 | 0.00 |
| | | | | 2.0 | 50.0 | 2.76 |
| | | | | 5.0 | 47.0 | 4.18 |
| | | | | 10.0 | 43.0 | 4.23 |
| Formula III: (a=8, R=CH$_3$, b=15, c=1.5) Formula III: (a=8, mixed oxide adduct having order of addition of R=hydrogen b=10 and R=CH$_3$, b=5, c=1.5) | .1% | 100 | 44 | 1.0 | 49.0 | 0.00 |
| | | | | 2.0 | 47.0 | 0.00 |
| | | | | 5.0 | 45.0 | 0.00 |
| | | | | 10.0 | 25.0 | 1.15 |

While particular embodiments of the invention have been described, it is to be understood that such descriptions are presented for purpose of illustration only and that the invention is not limited thereto and that reasonable variations and modifications, which will be apparent to those skilled in the art, can be made without departing from the spirit or scope of the invention as defined by the following claims.

What is claimed is:

1. A composition of matter comprising an anionic perflurosubstituted compound having a representative formula selected from the group consisting of:

$$F(CF_2)_{\overline{a}}CH_2-CH_2-O-(CH_2-CH-O)_{\overline{b}}-(CH_2-CH-O)_{\overline{c}}-H \quad \text{Formula I}$$
$$\underset{R}{|} \quad \underset{CH_2}{|}$$
$$\underset{SO_3^- X^+}{|}$$

and $$F(CF_2)_{\overline{a}}CH_2-CH_2-O-(CH_2-CH-O)_{\overline{b}}-(CH_2-CH-O)_{\overline{c}}-H \quad \text{Formula II}$$
$$\underset{R}{|} \quad \underset{CH_2}{|}$$
$$\underset{Z_dSO_3^- X^+}{|}$$

wherein a is a whole number or fraction thereof in the range of from about 4 to about 18;
wherein b is a whole number or fraction thereof in the range of from about 0 to about 30;
wherein c is a whole number or fraction thereof in the range of from about 1 to about 3;
wherein d is independently a whole number or fraction thereof in the range of from about 0 to about 1 and the sum of the average values of d are less than or equal to c;
R is independently selected from the group consisting of hydrogen and a methyl group whereby mixtures containing both groups may result; and
X$^+$ is an exchangeable cation; and
Z is a nucleophile containing radical species containing at least one member selected from the group consisting of oxygen and nitrogen wherein the nitrogen is in the form of NR$^1$ wherein R$^1$ is independently selected from the group consisting of hydrogen and methyl radicals.

2. The composition of claim 1 wherein:
a is from about 6 to 12;
b is from about 0 to 20;
c is from about 1 to 2; and
the sum of the average values of d is from about 0 to 2.

3. The composition of claim 1 wherein:
a is from about 6 to 12;
b is from about 10 to 20;
c is about 1.5;
the sum of the average values of d is about 1.5; and
X is selected from potassium and ammonium ions.

4. The composition of claim 3 wherein:
a is from about 7 to 9 and
b is from about 15 to 20.

5. The composition of claim 4 wherein a is about 8.

6. A composition of matter represented by the formula:

$$F(CF_2)_{\overline{a}}CH_2-CH_2-O-(CH_2-CH-O)_{\overline{b}}-(CH_2-CH-O)_{\overline{c}}-H$$
$$\underset{R}{|} \quad \underset{CH_2}{\diagup}$$
$$O-C_6H_4-SO_3^- X^+$$

wherein a is a whole number or fraction thereof in the range of from about 6 to about 12;
wherein b is a whole number or fraction thereof in the range of from about 10 to about 20;
wherein c is a whole number or fraction thereof in the range of from about 1 to about 2;
R is independently selected from hydrogen and a methyl radical; and
X$^+$ is a cation selected from the group consisting of sodium, potassium and ammonium ions.

7. The compostion of claim 6 wherein:
a is from about 7 to about 9;
b is from about 15 to about 20; and
c is about 1.5.

8. The composition of claim 6 wherein a is about 8.

9. The composition of claim 8 wherein X is selected from the group consisting of potassium and ammonium ions.

10. A composition of matter represented by the formula:

$$F(CF_2)_{\overline{a}}CH_2CH_2-O-(CH_2-CH-O)_{\overline{b}}-(CH_2-CH-O)_{1.5}-H$$
$$\underset{R}{|} \quad \underset{CH_2}{|}$$
$$O-C_6H_4-SO_3^- X^+$$

wherein:

a is a whole number or fraction thereof in the range of from about 6 to about 12;

b is a whole number or fraction thereof in the range of from about 10 to about 20;

R is independently selected from hydrogen and a methyl radical; and

X+ is a cation selected from the group consisting of sodium, potassium and ammonium ions.

11. The composition of claim 10 wherein:
a is from about 7 to about 9;
b is from about 15 to about 20;
R is hydrogen; and
X is selected from the group consisting of potassium and ammonium ions.

12. The composition of claim 11 wherein a is about 8, d is about 1.5 and e is about 1.5.

13. The composition of claim 10 wherein:
a is about 8;
b is about 15 to 20;
R is hydrogen; and
X is selected from the group consisting of potassium and ammonium ions.

14. A sulfonic acid or salt product produced by the process comprising the steps of:

contacting a perfluoro alcohol of the formula

F(CF$_2$)$_a$CH$_2$CH$_2$OH wherein a is a whole number or fraction thereof of from 4 to 18 with an oxirane selected from the group consisting of ethylene oxide, propylene oxide, butylene oxide, mixtures thereof, and substituted derivatives thereof in the presence of a sufficient quantity of a Lewis acid catalyst in a reaction vessel in a manner so as to maintain a reaction temperature between 60° C. and 140° C. whereby a reaction product comprising a perfluoro alcohol-oxirane adduct containing from about 0 to about 30 moles of said oxirane is produced;

contacting said reaction product in a reaction vessel with an epihalohydrin in the presence of a sufficient quantity of a Lewis acid catalyst at a temperature within the range of from about 60° C. to about 100° C. whereby from 1 to 3 moles of said epihalohydrin are incorporated into said reaction product; and contacting said epihalohydrin-containing reaction product with a sulfonating agent in a reaction vessel under suitable conditions whereby said reaction mixture is caused to yield a sulfonic acid or salt of said epihalohydrin-containing reaction product.

* * * * *